United States Patent [19]

Fabian

[11] 4,311,496

[45] Jan. 19, 1982

[54] PRELIMINARY CONDENSATION OF METHANE IN THE FRACTIONATION OF A GASEOUS MIXTURE

[75] Inventor: Rainer Fabian, Geretsried, Fed. Rep. of Germany

[73] Assignee: Linde Aktiengesellschaft, Wiesbaden, Fed. Rep. of Germany

[21] Appl. No.: 135,556

[22] Filed: Mar. 31, 1980

[30] Foreign Application Priority Data

Mar. 30, 1979 [DE] Fed. Rep. of Germany ....... 2912761

[51] Int. Cl.³ .............................................. F25J 3/00
[52] U.S. Cl. ......................................... 62/17; 62/28; 62/31; 62/24; 55/68
[58] Field of Search .................... 62/17, 20, 24–28, 62/31; 55/68

[56] References Cited

U.S. PATENT DOCUMENTS

| | | | |
|---|---|---|---|
| 3,498,067 | 3/1970 | Ranke | 62/24 |
| 3,508,413 | 4/1970 | Pryor | 62/28 |
| 3,886,756 | 6/1975 | Allam et al. | 62/17 |
| 4,102,659 | 7/1978 | Martin | 62/17 |

*Primary Examiner*—Norman Yudkoff
*Attorney, Agent, or Firm*—Millen & White

[57] ABSTRACT

In the fractionation of a gaseous mixture, of hydrogen, methane, and carbon monoxide, comprising a cold methane wash to obtain a gaseous stream of hydrogen and a liquid stream of carbon monoxide and methane, the improvement wherein of the gaseous mixture prior to the methane wash is subjected to a continuous partial condensation at a temperature higher than the cold methane wash, thereby obtaining a gaseous phase fraction and a condensed liquid phase fraction; the gaseous phase fraction is conducted to the methane wash, and the condensed liquid phase fraction is conducted to a stripping column which produces a bottoms product stream of methane and an overhead product stream of hydrogen and carbon monozide. The continuous partial condensation can be conducted either in a single stage or in multiple stages.

11 Claims, 2 Drawing Figures

PRELIMINARY CONDENSATION OF METHANANE IN THE FRACTIONATION OF A GASEOUS MIXTURE

BACKGROUND OF THE INVENTION

This invention relates to a process for the fractionation of a gaseous mixture comprising hydrogen, methane, and carbon monoxide, with a methane scrubber operating at a low temperature.

In a conventional process of this type (*Hydrocarbon Processing*, November 1971, p. 164), whose details are incorporated by reference herein, the gaseous mixture, obtained by steam reforming of hydrocarbons and subsequent $CO_2$ separation, is cooled to a temperature of about 90° K. and subjected to a scrubbing operation with liquid methane. During this step, substantially CO-free hydrogen is obtained as the top product of the scrubbing column, whereas the carbon monoxide dissolved in the methane is withdrawn from the bottom of the column. The loaded scrubbing medium (methane) is thereafter regenerated in a $CO/CH_4$ distillation column and reintroduced into the scrubbing column. In the distillation column, carbon monoxide is obtained as the top product and it represents a further product of the process. The refrigeration required for regenerating the scrubbing medium is made available by a cycle wherein a part of the separated carbon monoxide is circulated. For this purpose, the carbon monoxide is compressed in a compressor, condensed in the bottom of the regenerating column (i.e., $CO/CH_4$ separating column), thereby heating up the bottom, expanded, and reintroduced into the regenerating column as a recycle stream.

The methane obtained in this conventional process in the bottom of the regenerating column is, insofar as it exceeds the requirements of the methane scrubbing column, vaporized and removed as a byproduct gas together with gases obtained at other locations in the process.

The conventional process is advantageously employed for the fractionation of a gaseous mixture having a relatively low methane content, usually below 5%. In this process, the separated methane can be utilized to a large extent to compensate for scrubbing medium losses. However, if a gaseous mixture having a higher methane content is to be fractionated, then the consequence is a large additional expenditure for the $CO/CH_4$ separation in the regenerating column and thus a greatly increased expense for the carbon monoxide refrigeration cycle.

SUMMARY OF THE INVENTION

Accordingly, it is a primary object of this invention to provide a fractionating system of the aforementioned type wherein the fractionation of gaseous mixtures having relatively high methane contents can be conducted with minimum energy costs.

Upon further study of the specification and the appended claims, further objects and advantages of this invention will become apparent to those skilled in the art.

In the process of this invention, the gaseous mixture is initially continuously subjected to a partial condensation at a moderate temperature level, i.e., temperature higher than the methane wash, thereby producing a gaseous phase fraction and a liquid phase fraction. The gaseous phase fraction is then conducted to the methane wash, while the condensed fraction is conducted into a stripping column, wherein methane is recovered as the bottoms product and the overhead product comprises hydrogen and carbon monoxide.

The process of this invention takes advantage of the fact that most of the methane contained in the gaseous mixture condenses at a temperature higher than that required for the methane wash. The condensation takes place, for example, in the temperature range of between about 140° K. and 180° K. and, in individual cases, it is of course dependent on the pressure of the gaseous mixture.

The process of the present invention is applicable to raw feed gases comprising, by volume, 40% to 70%, of hydrogen; 0.1% to 15%, preferably 1% to 10% of carbon monoxide; and, 25% to 55%, preferably 30% to 50% of methane. Such feed gases can be obtained, for example, by the gasification of carbonaceous material.

The continuous preliminary condensation is conducted under substantially constant pressure (i.e., the pressure of the feed gas) until the gaseous effluent of the preliminary condensation step contains, by volume, 5% to 25%, preferably 7% to 20% of methane.

The term "continuous preliminary condensation" as used in this specification and the appended claims, is intended to cover preliminary condensation of methane from the feed stream until the concentration of methane in that stream reaches the values specified above. Thus, as would be apparent to those skilled in the art, "continuous preliminary condensation" is not necessarily intended to apply only to a process wherein the preliminary condensation is conducted for as long as the methane wash is in operation.

Since the condensed methane, at the equilibrium conditions contains only relatively small amounts of hydrogen and carbon monoxide dissolved therein, it is advantageous to separate the condensate from the remaining gaseous phase fraction at the medium temperature of the preliminary condensation (e.g., in a phase separator) and subsequently free the condensate in the stripping column from the accompanying hydrogen and carbon monoxide. The amount of energy expended for this separation is relatively minor and it is by far exceeded by the savings in energy realized because a large portion of the methane need no longer be conducted into the low-temperature section of the plant. The additional expenditures required for the apparatus for the treatment of the condensate (e.g. the stripping column) are, also, compensated for by savings in the low-temperature section of the plant because smaller structural components can now be used in this low-temperature section due to the reduced quantity of the gas to be processed.

The methane fraction separated at the moderate temperature in accordance with the process of this invention can be revaporized (e.g. by expansion) and since it is substantially free of carbon monoxide (not more than 0.1%, by volume) it can be fed into a supply network, for example SNG, i.e., synthetic natural gas.

The hydrogen and carbon monoxide dissolved in the condensed methane can be separated therefrom in the stripping column in a conventional manner, for example by heating the bottom of the stripping column or by introducing an inert stripping gas. The bottom of the stripping column is advantageously heated by passing the feed gas stream after the preliminary condensation, but before the phase separation, through a heating coil in the bottom of the stripping column, thereby condensing additional methane.

In the heating coil the temperature of the feed gas is reduced to about 140° K. to 150° K. After passing through the heating coil, the stream is conducted to the phase separator (discussed above) and then to the stripping column. It is especially advantageous to expand the condensate before it enters the stripping column to facilitate the separation. It is also advantageous to provide a heating unit in the bottom of the stripping column, which can be operated, for example, with raw gas, and which aids in desorbing the hydrogen and carbon monoxide from the condensed methane.

In a further aspect of the invention, the partial condensation of the gaseous mixture is conducted in several stages to thereby separate a maximally high proportion of the methane prior to its introduction into the low-temperature methane wash. For this purpose, the gaseous phase obtained in the first condensation stage is, after further cooling to the temperature of 120° K. to 130° K., preferably 124° K. to 128° K. again subjected to the phase separation and then conducted to a stripping column, wherein the newly formed methane-rich condensate is again freed of dissolved hydrogen and carbon monoxide. This mode of operation can be repeated in a multistage arrangement to separate additional methane. However, for economical considerations, it will generally be most advantageous to provide only two or three condensation stages. If more condensation stages are employed, the initial investment expenses for the additional condensation stages would probably be higher than the savings effected thereby in the low-temperature section, especially since with successive condensation stages the temperature of the condensate decreases with each stage and thus a larger proportion of hydrogen and carbon monoxide must be separated from the condensate. With the use of a two-stage condensation unit, however, the savings in the low-temperature section exceed by far the expenditures for the preliminary partial condensation section.

While the methane obtained in the bottom of the stripping column is practically free of impurities, the overhead or top product of the stripping column is enriched in hydrogen and carbon monoxide, but it also contains a considerable proportion of methane. To obtain valuable products of the process from this gas (i.e., methane, carbon monoxide and a hydrogen-enriched stream) according to this invention, this gaseous mixture is cooled to the low temperature of the methane wash (at least about 35° K., preferably 92° K.). During this cooling step, it is possible to condense out a large proportion (at last 99%) of the methane as well as a portion of the carbon monoxide (40% to 60%), whereas the hydrogen remains in the gaseous phase. After this cooling step, the cooled mixture is subjected to a phase separation, wherein a liquid condensate, comprising carbon monoxide and methane is separated from gaseous hydrogen. Subsequently, the liquid condensate, containing carbon monoxide and methane, can be separated, e.g., by rectification, into carbon monoxide and methane.

It is advantageous to subject the cooled top product of the stripping column to the phase separation step together with the fraction withdrawn from the bottom of the methane wash, after expansion of the latter. Since the expansion of the bottom product of the methane wash produces a flash gas containing a predominant proportion of hydrogen dissolved in the bottom product, a two-phase mixture is thus formed whose composition corresponds approximately to the cooled top product of the stripping column. Therefore, the cooled top product of the stripping column and the expanded bottom product of the methane wash are combined and can be processed together. Thus, the combined stream comprising the flash gas formed during the expansion of the bottom product of the methane wash and the gaseous top product of the stripping column is conducted to a conventional phase separator wherein the gas is separated and withdrawn as a single hydrogen-rich residual gas also containing carbon monoxide and methane. The residual gas can be used, for example, as a fuel gas. The composition of this gas is 65% to 85%, preferably 70% to 80% $H_2$, 20% to 35, preferably 20–30% CO and 1% to 3%, preferably 1% to 2% $CH_4$. The liquid fraction obtained in the phase separator, comprising, in addition to methane and carbon monoxide, only minor amounts of hydrogen, can then be fractionated in a conventional rectifying column into a methane fraction and a carbon monoxide fraction. The composition of the liquid fraction obtained in the phase separator is 55% to 80%, preferably 60% to 70% of $CH_4$, 20% to 40%, preferably 25% to 35% of CO, and 0.1% to 2%, preferably 0.1% to 1% of $H_2$. A portion of the methane fraction from the rectifying column is utilized for the methane wash, while the remainder thereof is withdrawn as an additional product of the process and, after warming, can also be fed into a pipeline such as, e.g., SNG.

It is, of course, also possible to conduct the process of this invention in the presence of other gaseous components in the raw feed gas, e.g., nitrogen, argon, ethane helium. Such gases will then appear in the individual product fractions (i.e., hydrogen, methane, carbon monoxide) in correspondence with their solution or condensation characteristics, as would be apparent to those skilled in the art, without substantially altering the course of the process of this invention.

Additional details of the process of this invention will be described below with reference to two embodiments schematically illustrated in the figures.

DETAILED DISCUSSION

In the following discussion and in the remainder of the specification, unless otherwise indicated, all temperatures are in degrees Kelvin (°K.), all pressures are in bars and all compositions are in % by volume.

Figure 1:
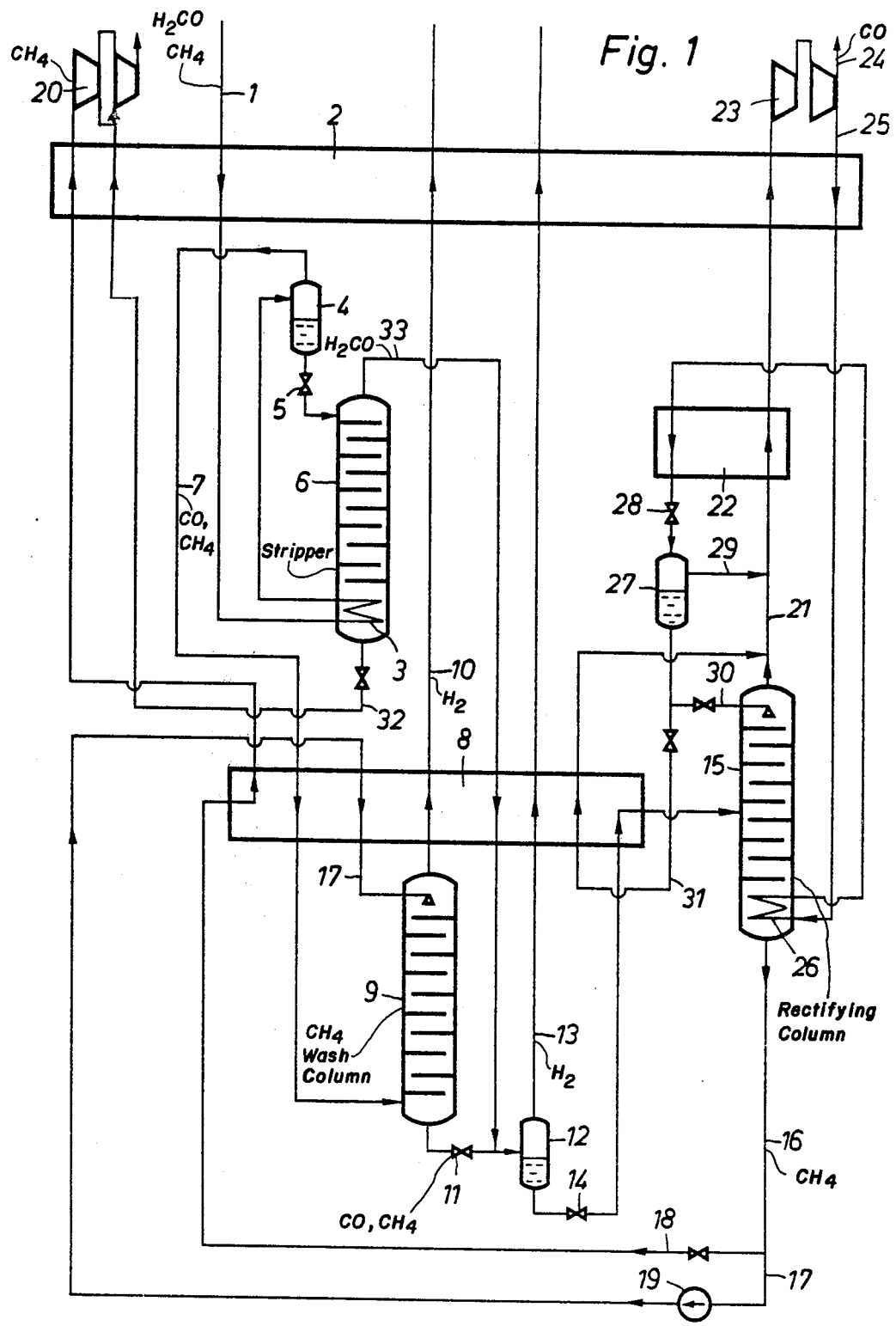
FIG. 1 illustrates an embodiment of the process of this invention operated with a single-stage continuous partial condensation at the medium temperature level.

In the embodiment of FIG. 1, a raw gas comprising 44 vol-% hydrogen, 7 vol-% carbon monoxide, and 49 vol-% methane, is fed under high pressure (e.g., 75 bars and a temperature of 308° K.) via conduit 1 into a heat exchanger 2 wherein it is cooled with fractionation products. During this step, a large proportion of the methane present in the raw gas is condensed therefrom. After the cooled gaseous mixture has passed through the heating coil 3 in the sump of a stripping column 6, thereby additionally condensing some of the methane entering the coil wherein it is further cooled, it enters a conventional phase separator 4. The liquid fraction separated in the separator 4, is expanded in an expansion valve 5 to a medium pressure, and thereafter is fed into the upper section of a stripping column 6.

The hydrogen and carbon monoxide impurities, which are troublesome in the SNG, are removed from the condensate of the separator 4 by a raw-gas-heated heating coil 3, which forces these impurities to exit as an overhead product of the stripping column 6. The separated bottom product represents quantitatively about one-half of the amount of the methane contained in the raw gas. This product is withdrawn via a conduit 32, vaporized in the heat exchanger 2, warmed, and then fed into a medium pressure stage of the compressor 20.

The top product of the stripping column 6, containing in addition to hydrogen and carbon monoxide, a substantial amount of methane is withdrawn via conduit 33 and cooled in the heat exchanger 8 to the temperature of the methane wash column 9. Since during this step substantially all of the methane, as well as a portion of the carbon monoxide, are condensed, the cooled mixture is subsequently combined with the bottom product of the methane wash, expanded in a conventional expansion valve 11 and conducted into a conventional liquid-gas separator 12.

The fraction obtained in the gaseous phase in the separator 4 is conducted through a conduit 7 to a heat exchanger 8 wherein cooling takes place to the low temperature (92° K.) of the methane wash. In the heat exchanger 8, substantially all of the remaining methane, and a portion of the carbon monoxide contained in the raw gas are condensed. The cooled-off gas withdrawn from the heat exchanger 8 at about 92° K. is introduced into the lower section of a scrubbing column 9 wherein the carbon monoxide is washed out of the gaseous phase by a subcooled, pure methane. At the top of the scrubbing column 9, there is thus obtained a purified hydrogen fraction which is discharged via a conduit 10, warmed in the heat exchangers 8 and 2, and then withdrawn as a product stream. This hydrogen product stream comprises, e.g., by volume 97% to 99% of hydrogen, and 1% to 3% of methane.

In the bottom of the scrubbing column 9 there is obtained a mixture which contains the entire dissolved carbon monoxide, the methane condensed in the exchanger 8 from the gaseous fraction of the separator 4, the methane utilized as the scrubbing medium, as well as a small proportion of dissolved hydrogen. The bottom product is withdrawn and expanded in an expansion valve 11 to a medium pressure, whereby the dissolved hydrogen is substantially completely released from the liquid and it is then separated in the subsequent conventional phase separator 12.

The hydrogen-enriched flash gas obtained in the separator 12 is withdrawn via a conduit 13, warmed in the heat exchangers 8 and 2, and discharged; it can be used, for example, as a fuel gas. The liquid fraction remaining in the separator 12 is further expanded in a conventional expansion valve 14, then partially vaporized in the heat exchanger 8, and fed into the middle section of a rectifying column 15. In the rectifying column 15, the carbon monoxide-methane mixture is fractionated into a substantially pure methane fraction obtained in the bottom of the column and into a substantially pure carbon monoxide fraction obtained as the top product. The methane stream from the bottom is withdrawn via a conduit 16 and divided into two substreams 17 and 18. The partial stream 17 is used as the scrubbing liquid necessary for the methane wash 9. This stream is pressurized by a pump 19 to the pressure of the methane wash (about 74 bars) and, after subcooling in the heat exchanger 8 to the temperature of the methane wash, is introduced to the upper section of the scrubbing column 9 as the scrubbing liquid. The other partial stream 18 comprises excess methane which is vaporized in the heat exchanger 8, warmed in the heat exchanger 2, and discharged as the methane product stream of the process. Since this process gas is under a relatively low pressure, generally between 1 and 3 bars, it is compressed in a compressor 20 to the pressure of a natural gas network, i.e. normally to the pressure of between 30 and 80 bars.

The carbon monoxide obtained at the top of the rectifying column 15 is withdrawn via a conduit 21, warmed in the heat exchangers 22 and 2, and passed into a compressor 23. The product carbon monoxide stream can be withdrawn from the compressor 23 via a conduit 24 at a desired pressure level (e.g., 2 bars to 30 bars). The compressor 23 is used for a refrigerating cycle to produce the refrigeration necessary for the rectifying column and for cooling the gas of conduits 7 and 33 in the heat exchanger 8. For this purpose, a partial stream of carbon monoxide is conducted in a cycle via a conduit 25, it is then cooled in the heat exchanger 2, then condensed in the bottom of the rectifying column 15 in the heater coil 26, thereby simultaneously producing rectification vapour. Thereafter this partial stream is subcooled in the heat exchanger 22 against product carbon monoxide, and expanded through an expansion valve 28 into a carbon monoxide collecting tank 27. The flash gas formed during the expansion in the valve 28 passes via a conduit 29 directly into the product line 21 and is rewarmed together with the overhead product of the rectifying column 15. The liquid from the carbon monoxide collecting tank 27 serves in part as a reflux 30 for the rectifying column 15 which is introduced into the rectifying column 15 in the upper section, and in part, as a refrigerant conducted to the heat exchanger 8 via a conduit 31.

If, as in the present example, the pressure of the raw gas is high, for example at least 70 bars, and a methane content in the raw gas is also relatively high, e.g., no less than 30% by volume, the Joule-Thomson effect occurring during the expansion valves 5, 11 and 28 of the gaseous mixture is generally so substantial that there is no need for a separate refrigerating plant for cooling the raw gas to the medium temperature level required in the stripping column 6. However, if the amount of cooling provided by the expansion valves is insufficient, additional cooling can be provided in a conventional manner in the heat exchanger 2 by the installation of a conventional refrigerating plant at a relatively high temperature level.

Figure 2:
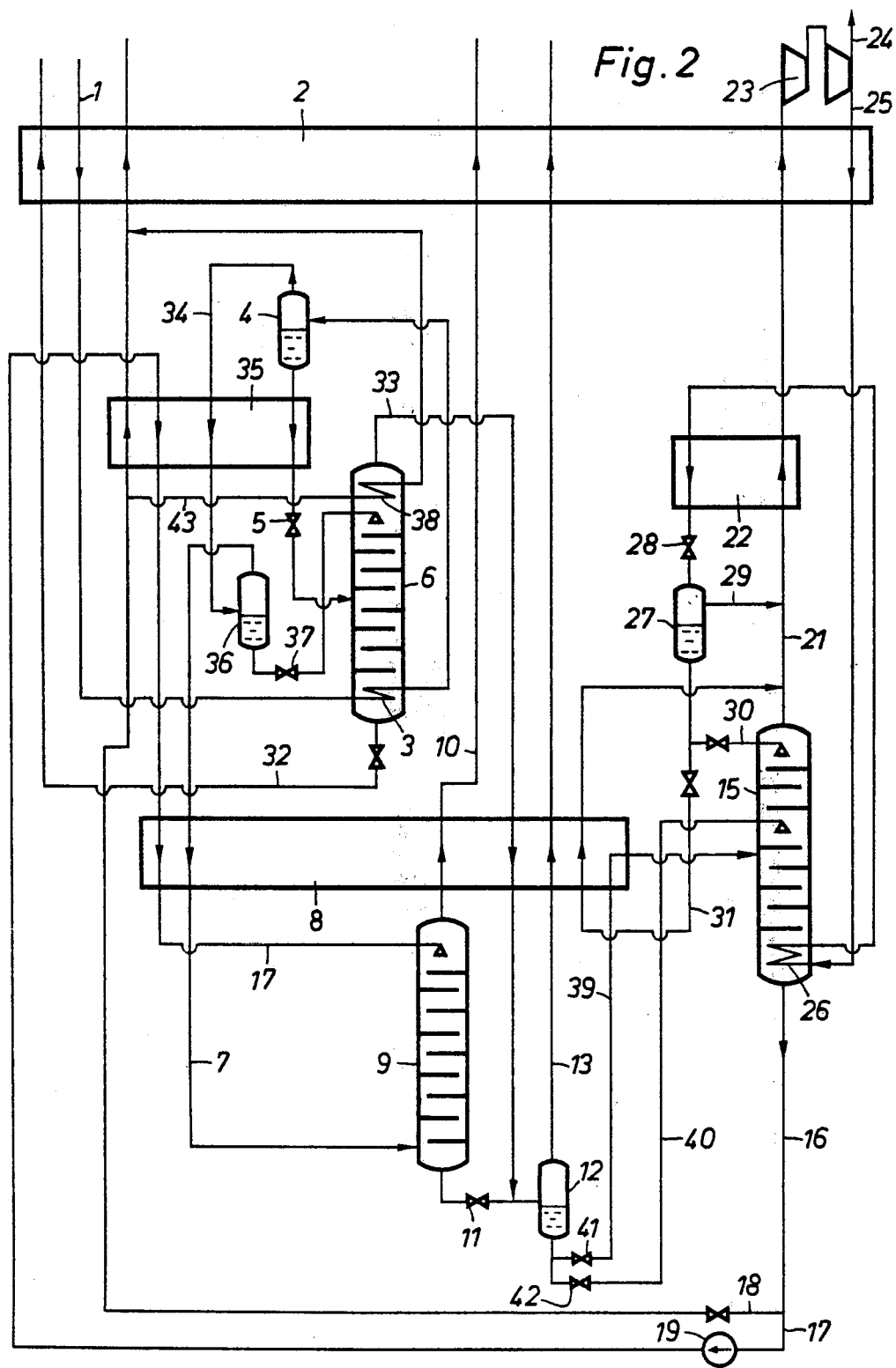
FIG. 2 illustrates another embodiment of the process of this invention operated with a two-stage continuous partial condensation at the medium temperature level.

In the embodiment shown in FIG. 2, 100,000 Nm$^3$/h of a raw gas is introduced into the process through a conduit 1 under a pressure of 75 bar and at a temperature of 308° K. This gas contains 44 vol-% hydrogen, 7 vol-% carbon monoxide, and 49 vol-% methane. After cooling in a heat exchanger 2 and in the bottom heater 3 of a stripping column 6, 42,000 Nm$^3$/h of condensate as well as 58,000 Nm$^3$/h of a gaseous fraction are obtained in conventional liquid-vapor separator 4. The condensate comprises by volume 84% methane, 9% hydrogen and 7% carbon monoxide. The gaseous fraction comprises by volume 69% hydrogen, 24% methane and 7% carbon monoxide. The temperature of both fractions is about 147° K. The gaseous fraction from the separator 4 is fed via a conduit 34 into a heat exchanger 35 wherein it is further cooled at 128° K., and during this step another 11,000 Nm³/h of the gaseous mixture is condensed. In a conventional liquid-vapor separator 36, a second phase separation is conducted to separate 11,000 Nm³/h of the condensate, comprising 82% methane, 9% hydrogen and 9% carbon monoxide, from 47,000 Nm³/h of the gaseous fraction comprising 83% hydrogen, 6% carbon monoxide and 11% methane.

As would be apparent to those skilled in the art, the condensates from the separators 4 and 36 are introduced into a stripping column 6 at separate feed points in accordance with the respective equilibrium conditions of the stripping column and of the condensate streams. Thus, the condensate from the separator 4 is first subcooled in a heat exchanger 35 to a temperature of 128° K. and then, after expansion in a throttle valve 5, to a pressure of 7.5 bars is introduced into the middle section of the column 6. The condensate from the separator 36, after expansion in a throttle valve 37 to the pressure of the stripping column 6, is introduced into the upper section of the column.

The stripping column 6 is operated under a pressure of 7.5 bar and at temperatures of between 144° K. in the bottom and 128° K. at the top of the column. In this example, the stripping column 6 is additionally provided with a top cooler 38 to obtain recondensation of a portion of the methane contained in the top product and thus an increase in the methane yield in this process stage.

33,000 Nm³/h of substantially pure methane (at least 33.3% CH₄) is withdrawn from the bottom of the stripping column 6 and fed via a conduit 32 to the heat exchanger 2, where the methane is then present as a medium-pressure methane, at about 7.5 bars. This methane can, for example, be recompressed as indicated in the example of FIG. 1 and fed to a natural gas network. 20,000 Nm³/h of a gaseous fraction is withdrawn as the head product of the stripping column 6 through a conduit 33, which fraction comprises 55% methane, 25% hydrogen, and 20% carbon monoxide.

The remainder of the process of this example is conducted substantially in the same manner as the process described in FIG. 1, except for the differences noted below. One of the differences concerns the feed to the rectifying column 15, which in this case is effected by subdividing the condensate from the separator 12 into two partial streams 39 and 40 which are expanded through the valves 41, 42, respectively to the pressure of the rectifying column and then separately passed into the column. The partial stream 39, similarly to the process of FIG. 1, is fed after partial vaporization in the heat exchanger 8, into a middle section of the column 15. Conversely, the partial stream 40 passes directly into a higher-level section of the column 15.

A further difference resides in the treatment of the methane fraction 16 obtained at the bottom of the rectifying column 15, and which, as in the process of FIG. 1, is broken into two substreams 17 and 18. The partial stream 17, used for the methane wash, is first subcooled in the heat exchanger 35 to 128° K. and then further cooled to 90° K. in the heat exchanger 8, before being introduced to the scrubbing column as a scrubbing stream. The other substream 18 is not passed through the heat exchanger 8 (as in the process of FIG. 1) but is instead vaporized and then warmed to ambient temperature in the heat exchangers 35 and 2, respectively. Prior to the introduction of the substream 18 to the heat exchanger 2 to increase its temperature to ambient, a further partial stream 43 is branched off from the stream 18. This further partial stream 43 is vaporized in the top cooler 38 of the stripping column 6, and then recombined with the partial stream 18, which is then passed to the heat exchanger 2. This low-pressure methane stream 18 can then also be compressed, for example, in accordance with the embodiment of FIG. 1, and fed into a natural gas network.

The operational data for the course of the process of FIG. 2, following the continuous preliminary separation of the methane is set forth below.

In the methane wash 9, the gaseous mixture fed via conduit 7 is subjected to a scrubbing step with 11,000 Nm³/h of pure methane, having a temperature of 92.5° K. 39,000 Nm³/h of carbon-monoxide-free hydrogen is withdrawn through the conduit 10 of the methane wash 9. This product stream contains only 2% methane as an impurity. In the bottom of the scrubbing column, 19,000 Nm³/h of a liquid is obtained comprised of 79% methane, 16% carbon monoxide and 5% hydrogen. The temperature of the bottom of the column 9 is 95.5° K. The pressure of the methane wash column is about 7.5 bar.

After expansion of the bottom product in the expansion nozzle 11 to 7.3 bar and mixing the expanded gas with the top product of the stripping column 6, 6,600 Nm³/h of a flash gas is obtained in the separator 12 comprising 83% hydrogen, 14% carbon monoxide, and 3% methane, whereas the remaining liquid fraction of the separaor 12 (32,400 Nm³/h) comprises 80% methane, 19% carbon monoxide and 1% hydrogen. 25,800 Nm³/h of methane is obtained from the bottom of the rectifying column 15, 14,800 Nm³/h of which, after the separation of the wash methane, is withdrawn as the product of the process through the conduit 18 at a temperature of 126° K. and under a pressure of 2.5 bar.

A comparison with the amount of the methane obtained from the stripping column 6 through the conduit 32 shows that 69% of the separated methane is obtained in the preliminary separation at the medium temperature level (128° K.–147° K.), and that only 31% is separated at the lower temperature of the methane wash.

Finally, 6,600 Nm³/h of a carbon monoxide fraction is obtained as the top product of the rectifying column 15. This fraction comprises 92% carbon monoxide and 8% hydrogen.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the fractionation of a gaseous mixture comprised of hydrogen, methane, and carbon monoxide, comprising a methane wash conducted in a methane wash column at a relatively low temperature, the improvement comprising subjecting the gaseous mixture which contains at least 25% by volume of methane, prior to the methane wash, to a partial condensation at a temperature higher than the relatively low temperature of the methane wash, thereby obtaining a gaseous phase fraction and a condensed liquid phase fraction, additionally cooling the gaseous phase fraction, conducting the additionally cooled gaseous phase fraction to the methane wash, conducting the condensed liquid phase fraction to a stripping column which produces a bottoms product stream comprising methane and an overhead product stream comprising hydrogen, carbon monoxide and methane, and recovering methane from the bottoms of the methane wash column in a rectifying column distinct from the stripping column.

2. A process according to claim 1, wherein the stripping column is operated at a pressure lower than the methane wash.

3. A process according to claim 2, wherein the partial condensation comprises more than one stage.

4. A process according to claim 3, wherein each of the condensed liquid phase fractions from each of the initial partial condensation stages is conducted to a common stripping column.

5. A process according to claim 4, wherein the top product stream of the common stripping column is further cooled to the low temperature of the methane wash, thereby producing a partially-condensed stream.

6. In a process for the fractionation of a gaseous mixture comprised of hydrogen, methane, and carbon monoxide, comprising a methane wash conducted in a methane wash column at a relatively low temperature, the improvement comprising subjecting the gaseous mixture, prior to the methane wash, to a plural stage partial condensation at temperatures higher than the relatively low temperature of the methane wash, thereby obtaining gaseous phase fraction and plural liquid phase fractions, conducting the gaseous phase fraction to the methane wash, and conducting the plural condensed liquid phase fractions to a common stripping column which produces a bottoms product stream comprising methane and an overhead product stream comprising hydrogen and carbon monoxide, cooling said overhead product stream to the low temperature of the methane wash, thereby producing a partially-condensed stream, and recovering methane from the bottoms of the methane wash column in a rectifying column distinct from the stripping column.

7. A process according to claim 6 wherein the stripping column is operated at a pressure lower than the methane wash.

8. A process according to claim 5 or 6, wherein a liquid stream from the methane wash comprising methane and carbon monoxide is expanded, combined with the partially condensed stream, and the thus-combined stream is subsequently conducted to a phase separation step which produces a liquid fraction and a gaseous fraction, said liquid fraction being passed to said rectification column.

9. A process according to claim 2 or 7, wherein the top product stream of the stripping column is further cooled to the low temperature of the methane wash, thereby producing a partially condensed stream.

10. A process according to claim 9, wherein the liquid stream from the methane wash comprising methane and carbon monoxide is expanded, combined with the partially condensed stream, and the thus-combined stream is subsequently conducted to a phase separation step which produces a liquid fraction and a gaseous fraction, said liquid fraction being passed to said rectification column.

11. A process according to claim 10, wherein the liquid fraction is conducted to a rectifying column which produces a methane fraction and a carbon monoxide fraction.

* * * * *